(12) United States Patent
Nuotio

(10) Patent No.: US 9,720,007 B2
(45) Date of Patent: Aug. 1, 2017

(54) METHOD AND ASSEMBLY FOR TRANSPORTING SINGLE AND MULTIPLE REACTION VESSELS

(75) Inventor: Vesa Nuotio, Vantaa (FI)

(73) Assignee: Thermo Fisher Scientific Oy, Vantaa (FI)

( * ) Notice: Subject to any disclaimer, the term of this patent is extended or adjusted under 35 U.S.C. 154(b) by 285 days.

(21) Appl. No.: 13/824,167

(22) PCT Filed: Oct. 28, 2011

(86) PCT No.: PCT/FI2011/050949
§ 371 (c)(1),
(2), (4) Date: Apr. 26, 2013

(87) PCT Pub. No.: WO2012/056115
PCT Pub. Date: May 3, 2012

(65) Prior Publication Data
US 2013/0209210 A1    Aug. 15, 2013

Related U.S. Application Data

(60) Provisional application No. 61/408,051, filed on Oct. 29, 2010.

(51) Int. Cl.
*B65G 1/04* (2006.01)
*B01L 3/00* (2006.01)
(Continued)

(52) U.S. Cl.
CPC ............ *G01N 35/0099* (2013.01); *B01L 9/06* (2013.01); *B25J 11/00* (2013.01); *B25J 15/12* (2013.01); *B25J 15/04* (2013.01)

(58) Field of Classification Search
CPC .... G01N 2035/0099; B25J 15/04; B25J 15/12
See application file for complete search history.

(56) References Cited

U.S. PATENT DOCUMENTS 3,616,497 A * 11/1971 Esposito, Jr. ......... H01L 23/291
24/542
4,455,280 A    6/1984 Shinohara et al.
(Continued)

FOREIGN PATENT DOCUMENTS

EP    0 543 638 A1    5/1993
EP    1 647 826 A1    4/2006
(Continued)

OTHER PUBLICATIONS

European Patent Office, International Search Report and Written Opinion of the International Searching Authority, International Patent Application No. PCT/FI2011/050950, mailed Jan. 27, 2012 (12 pages).

*Primary Examiner* — P. Kathryn Wright
(74) *Attorney, Agent, or Firm* — Thompson Hine LLP

(57) ABSTRACT

A method and apparatus for transporting single and multiple reaction vessels. At least one reaction vessel is provided and at least one tray includes at least two seats for the at least one reaction vessel, and at least one gripper. One of the reaction vessel or the tray is engaged with the gripper at a first position. The gripped element is transported to a second position wherein the gripper is released. A gripping collar is provided both on the reaction vessel and the tray for the gripper to engage. At one transport stage one of the reaction vessel or the tray is engaged with the gripper at a first position by pushing the gripper from above to engage with the gripping collar and in a second stage the transported element is disengaged from the gripper by moving the gripper sideways in relation to the center axis of the gripping collar.

14 Claims, 8 Drawing Sheets

(51) Int. Cl.
  *G01N 35/00* (2006.01)
  *B01L 9/06* (2006.01)
  *B25J 11/00* (2006.01)
  *B25J 15/12* (2006.01)
  *B25J 15/04* (2006.01)

(56) References Cited

U.S. PATENT DOCUMENTS

| | | | |
|---|---|---|---|
| 5,479,969 A * | 1/1996 | Hardie | B65B 3/003 |
| | | | 141/103 |
| 5,578,494 A | 11/1996 | Clark et al. | |
| 5,628,962 A | 5/1997 | Kanbara et al. | |
| 5,862,934 A | 1/1999 | Sattler et al. | |
| 6,060,022 A | 5/2000 | Pang et al. | |
| 6,265,225 B1 | 7/2001 | Otto et al. | |
| 6,458,324 B1 | 10/2002 | Schinzel | |
| 6,866,820 B1 | 3/2005 | Otto et al. | |
| 7,717,284 B2 | 5/2010 | Giusti | |
| 2001/0028863 A1 | 10/2001 | Kitagawa | |
| 2006/0228262 A1 | 10/2006 | Jacobs et al. | |
| 2009/0117004 A1 | 5/2009 | Fritchie et al. | |
| 2013/0118118 A1 | 5/2013 | Kubler et al. | |

FOREIGN PATENT DOCUMENTS

| | | |
|---|---|---|
| EP | 2 191 942 A1 | 6/2010 |
| JP | 2003-128242 | 5/2003 |
| JP | 2005061897 A | 3/2005 |

\* cited by examiner

METHOD AND ASSEMBLY FOR TRANSPORTING SINGLE AND MULTIPLE REACTION VESSELS

FIELD OF THE INVENTION

The present invention relates to a method and apparatus for transporting a single reaction vessel and a tray for multiple reaction vessels for use in an automated chemical analyzer.

BACKGROUND OF THE INVENTION

In hospitals and laboratories, several chemical and diagnostic analyses are done by automatic analyzing equipment. The level of automation varies, but the present trend is to streamline the analyzing work as much as possible. As many more complicated analyzes must be done by highly educated laboratory personnel involving a lot of manual work, the productivity and throughput of a laboratory and individual analyzers has been low. If the automation rate is increased, more of the work can be performed automatically inside the automatic system without involvement of highly skilled personnel. Ideally, laboratory assistants simply load samples in racks into the analyzing apparatuses and laboratory chemists and biologists may concentrate on interpretation of the results and managing the operation of the laboratory. Such a system provides a good throughput combined with high certainty and quality of the work.

In order to enable the high rate of automation, many automated features are needed. One of the features is reliable management of sample liquids, reagents and other fluids needed for the operation of the analyzer. This involves sample vessels, reagent vessels and reaction vessels and means for transferring them within the automated analyzer. Another particularly important feature when the automated analyzer handles sensitive samples and/or utilizes volatile reagents is the use of a capped reaction vessel. However, capped reaction vessels introduce an additional mechanical problem when used on-board automated instrumentation: they must be automatically opened and closed. The following patent documents disclose some of the typical systems currently used in the art.

U.S. Pat. No. 6,589,789 shows an apparatus with two grippers, one for standard test tubes and one for the container that holds them. In here two grippers are needed, which evidently makes the apparatus complicated and expensive. U.S. Pat. No. 5,775,755 has a gripper that is used for transferring standard test tubes. Herein the test tubes are grabbed from above with four jaws that have a coated surface that provides sufficient friction to hold the tubes when they are lifted from a rack and moved. The gripper is tailored for test tubes.

SUMMARY OF THE INVENTION

The present invention provides a simple and reliable method and assembly for transporting a single reaction vessel as well as for transporting a tray containing several reaction vessels loaded on the tray. The invention also provides a gripper to be used in the method and assembly.

One embodiment of the invention provides a method wherein a single gripper can be used for transporting a single reaction vessel as well as trays of reaction vessels.

The body of the reaction vessel has a gripping collar that surrounds the opening of the vessel. The gripping collar is preferably circular and has the same or larger diameter as the lid of the vessel. A tray for handling two or more reaction vessels has a pod that has a similar gripping collar as the reaction vessel so that they can be handled with a same gripper.

Other objects and features of the invention will become apparent from the following detailed description considered in conjunction with the accompanying drawings. It is to be understood, however, that the drawings are intended solely for purposes of illustration and not as a definition of the limits of the invention, for which reference should be made to the appended claims.

DETAILED DESCRIPTION OF THE INVENTION

Figure 1:
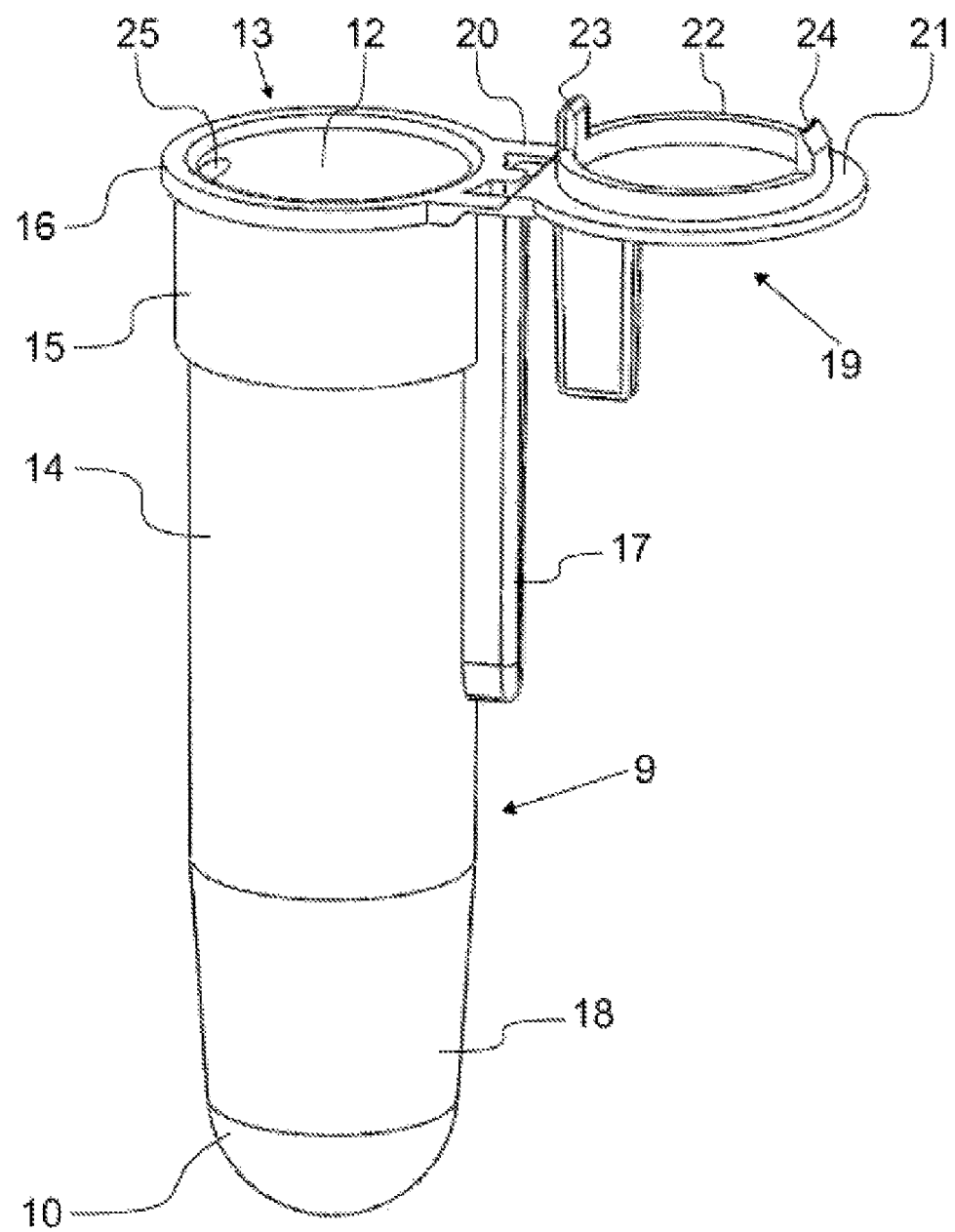
FIG. 1 is a side plan view of an exemplary reaction vessel that can be transported using one embodiment of the gripper of the present invention.

One embodiment of the reaction vessel that can be handled using the gripper of the present invention is depicted in FIG. 1. The reaction vessel 9 depicted in FIG. 1 is a tube-like vessel having an inner surface 12 defining the inner volume of the vessel 9. The diameter of the reaction vessel 9 can be constant from the opening 13 to the closed end 10. Alternatively, the internal and/or external diameter of the reaction vessel 9 can vary along the longitudinal axis of the reaction vessel 9. For example, the internal and/or external diameter can decrease gradually or at one or more fixed points along the longitudinal axis of the reaction vessel 9.

The inner surface 12 of the reaction vessel 9 forms an opening 13 at one end of the vessel 9. The outer surface of the vessel 9 forms its outer contour and comprises a cylindrical body part 14 having a stopping collar 15 at the same end as the opening 13 of the vessel 9 and a gripping collar 16 at the same end and surrounding the opening 13 of the vessel 9. The diameter of the gripping collar 16 is preferably the same or smaller than the diameter of the lid 19 so that a gripper (not shown) can be pushed over the lid 19 and the collar 16 from above (from the side of the lid) to grip the edge of the gripping collar 16. The preferred cross section of the gripping collar 16 is circular and the lid 19 should have a complimentary form to the gripping collar 16 to ensure their compatibility. In this case, the jaws of a gripper used for handling the vessels 9 can be made as a sector of a circle having the same diameter.

Further, the outer surface of the reaction vessel 9 can include a guide rail 17 extending along all or a part of the outer surface of the reaction vessel 9 and parallel to its longitudinal axis.

The end of the reaction vessel 9 opposite to the opening is closed and, according to one embodiment, is herein formed of a conical taper 18 ending at a spherical closed end 10. The inner surface of the vessel 9 follows this form. The function of the spherical closed end 10 is to concentrate the last remaining liquid to the center of the vessel 9 wherein it can be collected by a needle of a pipette or other similar device.

One important feature of the reaction vessel 9 is the lid 19. The main body of the lid 19 is a circular plate having a closing surface 21 that is adapted to set on top of the opening 13 of the vessel 9 and the gripping collar 16 when the lid 19 is in a closed position. The circumference of the body of the lid 19 corresponds with the outer circumference of the gripping collar 16. According to one embodiment, the inside of the lid 19 includes a guide ring 22 with guide pegs, one 23 of which is on the side of the hinge 20 and the other 24 of which is on the opposite side of the lid 19. The peg 24 farther from the lid 19 can be beveled.

The lid 19 comprises a hinge 20 connecting it to the body of the reaction vessel 9. According to one embodiment, the hinge 20 connects the lid 19 to the gripping collar 16 on the body of the vessel 9. On the inner surface 12 of the reaction vessel 9 and opposite to the hinge 20 is a knob 25 that is arranged to contact and engage the beveled peg 24. These elements may be arranged to opposite parts, so that peg 24 includes the knob 25 and the inner surface includes a corresponding dent (not shown).

The edge of the inner surface 12/opening 13 of the reaction vessel 9 is also beveled to lead the guide ring 22 inside the opening 13. When closed, the beveled peg 24 and knob 25 hold the lid 19 closed and the lid 19, guide ring 22 and the opening 13 can be dimensioned so that the required level of tightness is achieved between the components. The lid 19 can be liquid tight, gas tight or just provide a sufficient closure of the vessel 9 that prevents excessive evaporation.

The outer surface of the main body of the lid 19 comprises a circular flat surface 32 and a guide rod 26 extending away therefrom. According to one embodiment, the guide rod 26 is arranged between the centre point of the lid 19 and the hinge 20 connecting it to the reaction vessel 9. The purpose of the guide rod 26 will be clarified below. The guide rod 26 extends preferably upwards from the flat surface 32 of the lid 19 and so that it does not reach over the circumferential edge of the lid 19. This requirement is simply reasoned by the fact that if the guide rod 26 extends horizontally further than the other dimensions of the vessel 9, the vessel 9 needs more space sideways.

The reaction vessel 9 described herein is only one possible embodiment that can be used for implementation of the invention. For example, the guide rail 17 can be replaced by any form made on the outer surface of the vessel 9 that prevents rotation of the vessel 9. Examples of alternative forms made on the outer surface of the vessel 9 include two or more guide rails 17, a rectangular or other angular form on the outer surface of the vessel 9, or one or more grooves within the outer surface of the vessel 9. Further, the collars 15, 16 can be formed to perform the desired function. The collars have preferably a circular cross section and are formed as cylinders. However, rectangular, diamond shaped or other polygonal shape of cross section can also be used. The vessel 9 itself may have any desired inner or outer design; so long as it has a volume for liquid and an opening 13 that can be closed by a lid 19.

The hinge 20 of the lid 19 can be made as a separate piece and/or using a separate material or simply be formed as a single piece of the same material as the vessel 9 and lid 20 themselves. Preferably, the lid 19 and the vessel 9 are made as a single piece, for example by injection molding. In this embodiment, the flat surface 32 of the lid 19 operates as one guide surface and the guide rod 26 as another guide surface. Alternatively, there may be separate guide surface on the flat surface 32 of the lid 19 and the guide rod 26 may have a different form. One example of this will be described below. The relative placement of the guide rod 26 in view of the lid 19 and the hinge 20 may vary.

The purpose of closing the reaction vessel 9 is, firstly, to prevent evaporation and enrichment of a liquid therein. Secondly, closing of the vessel 9 prevents contamination of the contents and prevents spilling if the vessel 9 is dropped. The operation of the reaction vessel 9 and the opening and closing apparatus is described below to show how opening and closing of the reaction vessel 9 is achieved according to the invention.

An alternative embodiment of the vessel 9 has a lid 19 including a push ridge and the guide rod 26 is formed as a hook.

Figure 2:
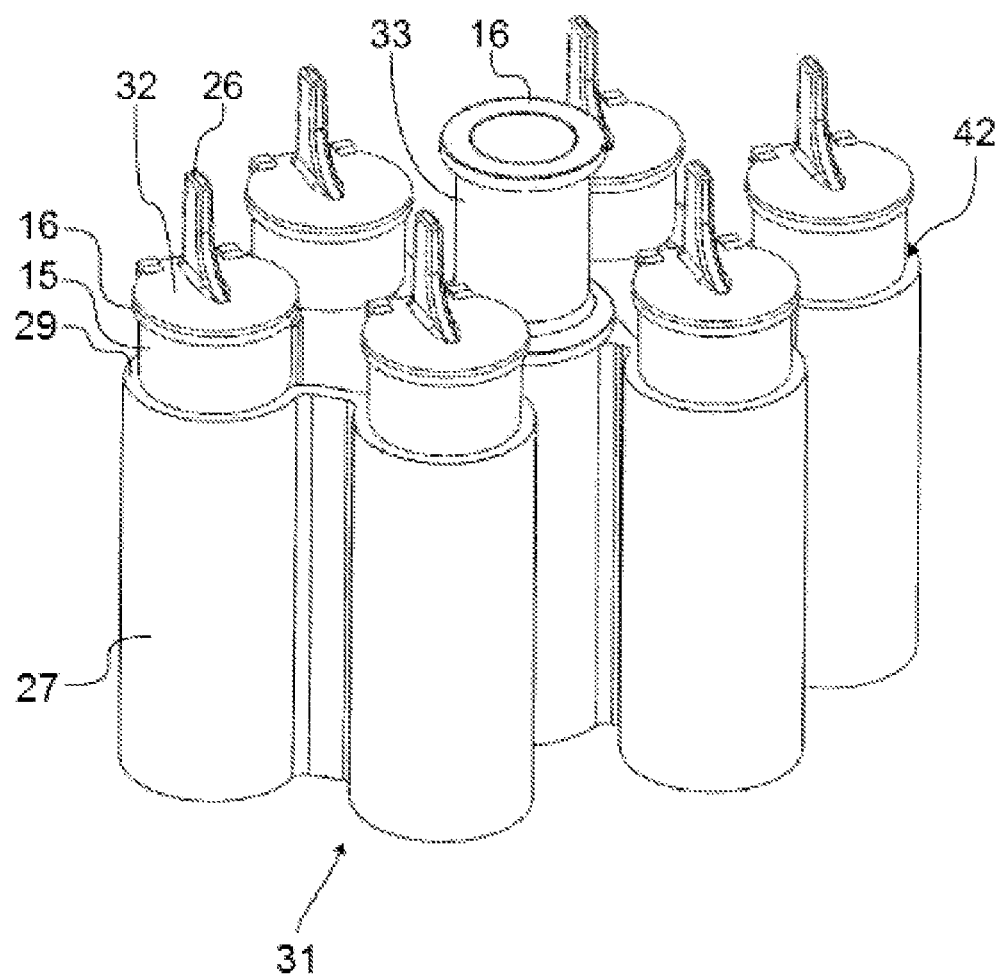
FIG. 2 is a side plan view of a tray for reaction vessels according to one embodiment of the present invention.

FIG. 2 discloses one embodiment of a tray 31 for transporting up to six reaction vessels 9. The tray 31 has six tubular seats 27 connected with walls 28. Each seat 27 has a cavity 42 wherein a reaction vessel 9 can be seated and a top surface 29. Each cavity further includes a guide slot (not shown) to accommodate the guide rail 17 of reaction vessel 9 and to lock the rotational position of the vessel 9, preventing the vessel 9 from rotating about its own axis. The diameter of the cavity 42 is preferably dimensioned so that it is smaller than the diameter of the stopping collar 15. The position of the stopping collar 15 sets the depth of the vessel 9 in the tray 31. When the vessel 9 sits in the seat 27, the gripping collar 16 of the vessel 9 is placed above the top surface 29 of the tray 31 (or seat 27) at a distance from the top surface 29 that corresponds with the width of the stopping collar 15. This width can be chosen by a designer.

The tray 31 has been designed to be symmetric, having an equal number of seats 27, for example three seats 27, on each side of a middle line. In the middle of the sets of three seats 27 is a tubular pod 33 for transporting the tray 31. This pod 33 comprises a tubular body 33 extending upwards from the tray 31. The tubular body 33 has a diameter that corresponds with the diameter of the stopping collar 15 and the tubular body 33 has a gripping collar 16 at the end of the pod 33. The diameter and thickness of the gripping collar 16 of the tray 31 correspond to the diameter and thickness of the gripping collar 16 of the reaction vessel 9. The distance of the gripping collar 16 of the pod 33 from the top surface 29 of the tray 31 is longer than that of the width of the stopping collar 15 of the vessels 9, giving thereby space to engage and disengage a gripper 44 from the pod.

It is clear that the tray 31 may have several different embodiments. For example, the number of the seats 27 is not limited, but it would be useless to have less than two seats 27. The features required for implementation of the invention are a top surface 29 connecting to a stopping means of a reaction vessel 9 and a pod 33 for a gripper 44 that has similar gripping collar 16 as the gripping collar 16 of the reaction vessels 9 that are handled by the gripper 44.

Figure 8:
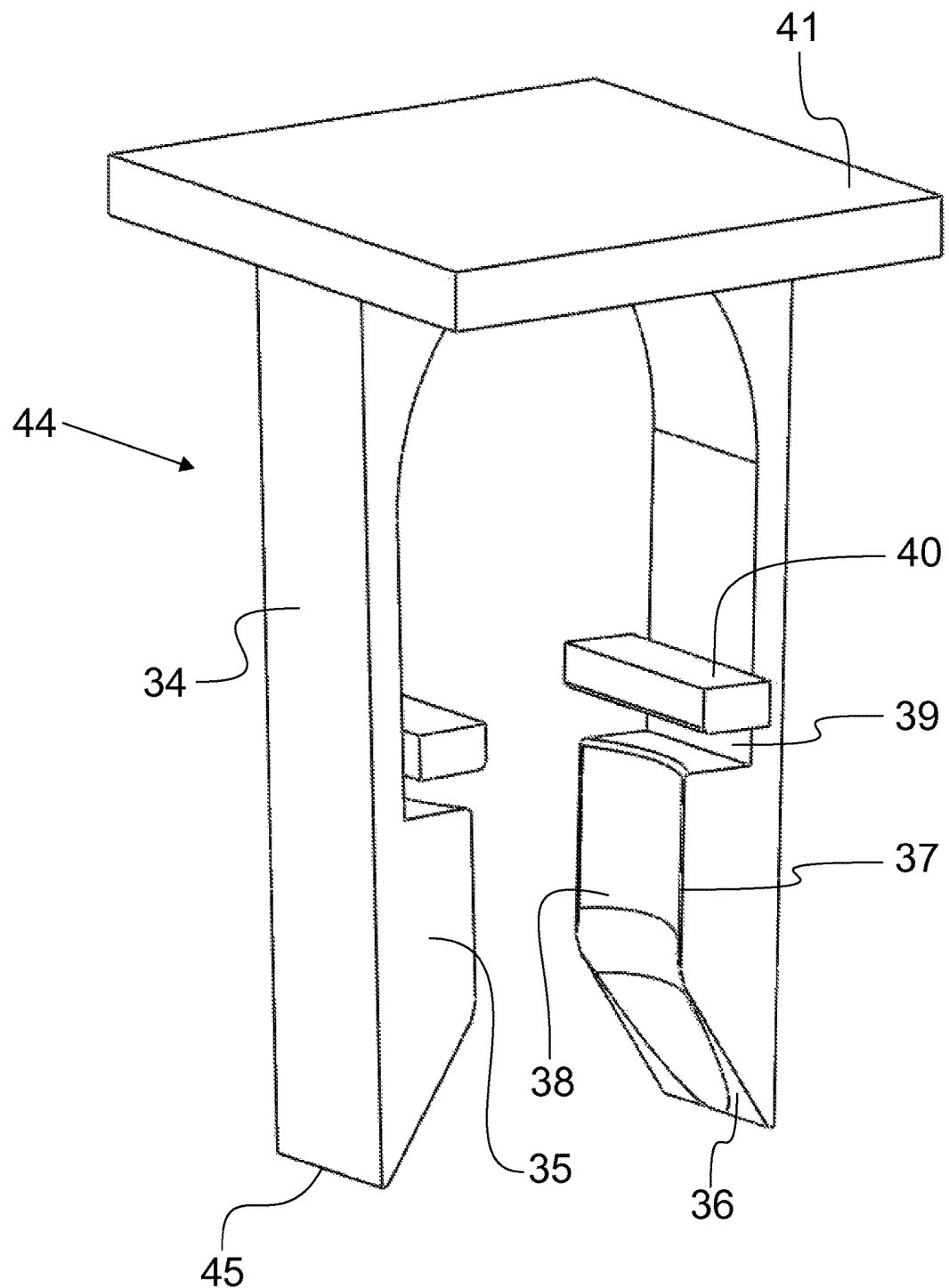
FIG. 8 is a side plan view of a reaction vessel of FIG. 1 with a gripper of FIG. 3 according to one embodiment of the invention.

One embodiment of a suitable gripper 44 is presented in FIG. 8. The gripper 44 has a body 41 wherefrom extend two symmetrically arranged hands 34 that have locking extensions 35 at their ends that are opposite to the body 41. The extensions 35 face towards each other and towards the central axis of the gripper 44. At the very end of the hands 34, the extensions 35 have a beveled surface 36 so that the tip 45 of the hand 34 is sharp and the extensions 35 move towards each other according to the bevel angle. The beveled surface 36 ends at a surface 37 that is parallel to the outer surface of the hands 34. Both the beveled surface 36 and the parallel surface 37 have a concave groove 38 starting from the tip 45 of the hand 34. The curvature of this groove 38 has preferably the same curvature and diameter as the stopping collar 16 of the tray 31 and the stopping collar 16 of the vessel 9. Alternatively, the groove 38 may have some other form, for example oval or V-shape. The hands 34 must have at least one open space between them in order to enable sideways movement of the pod 33 of the tray 31 or a vessel 9 between them. According to the embodiment depicted in FIG. 8, the hands 34 have two opposing open spaces between them.

The parallel surface 37 ends at a groove 39 that is limited on the side of the body 41 by stoppers 40. The groove 39 is dimensioned either according to the width of the gripping collar 16 or the combined width of the gripping collar 16 and the lid 19 together. If it is desirable to hold the lid 19 closed with the gripper 44, the later combined dimensioning is useful.

Figure 4:
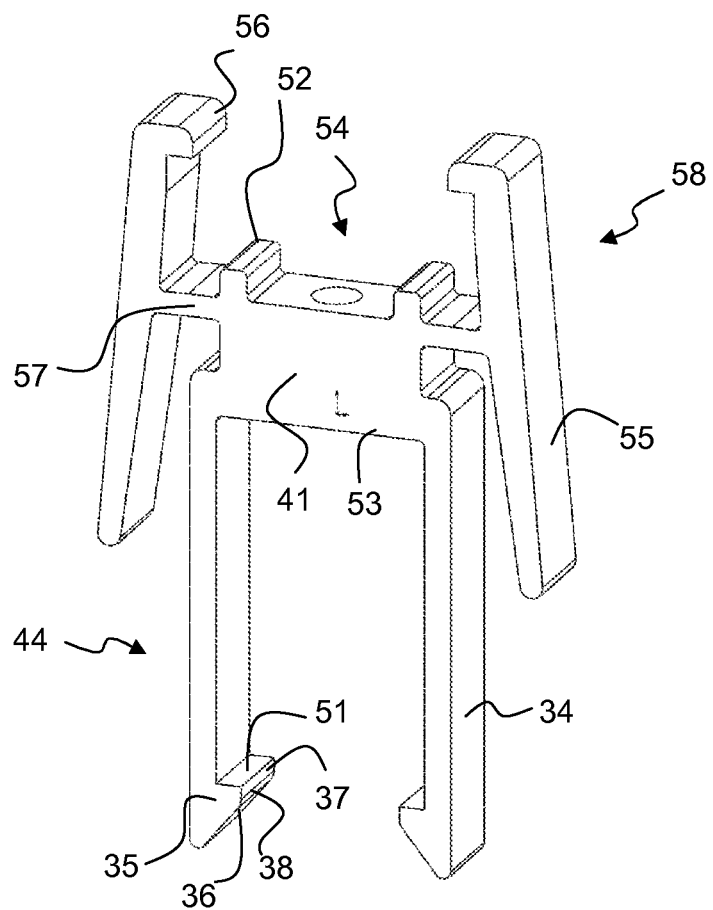
FIG. 4 shows an embodiment of a changeable gripper.
Figure 5:
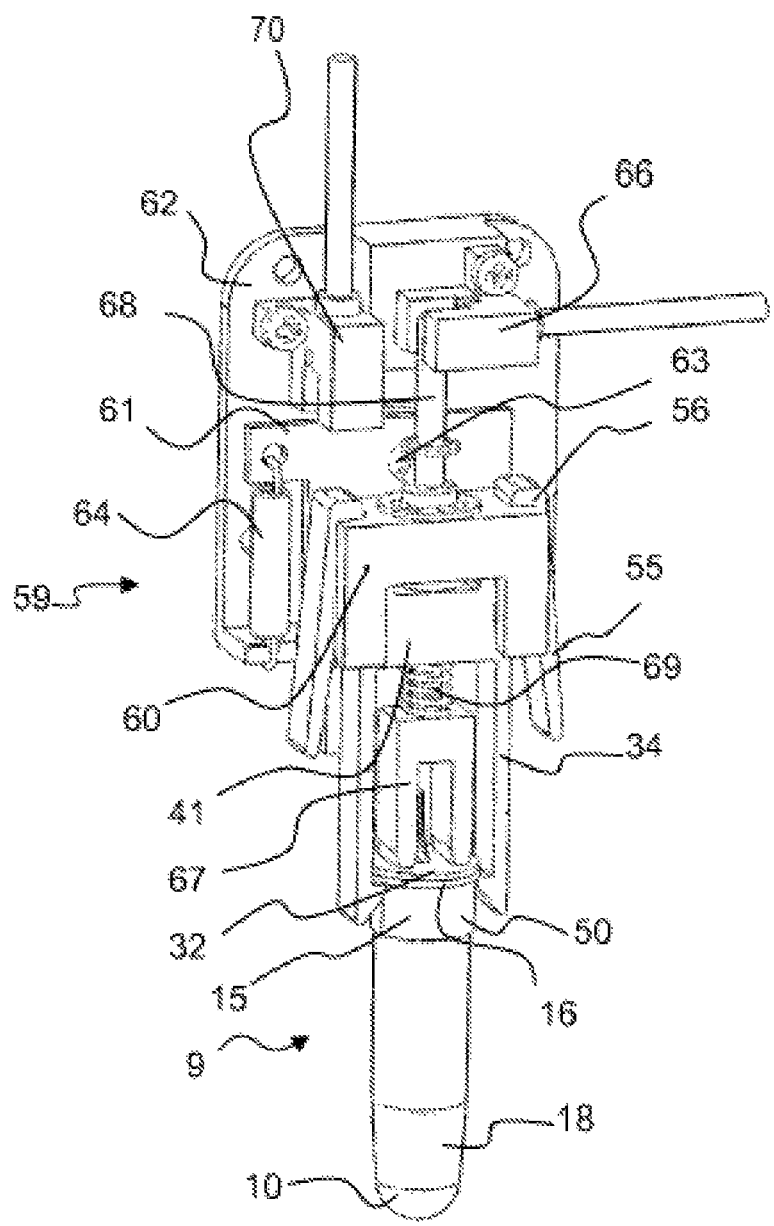
FIG. 5 shows a side view of a changeable gripper attached to a robot arm.
Figure 6:
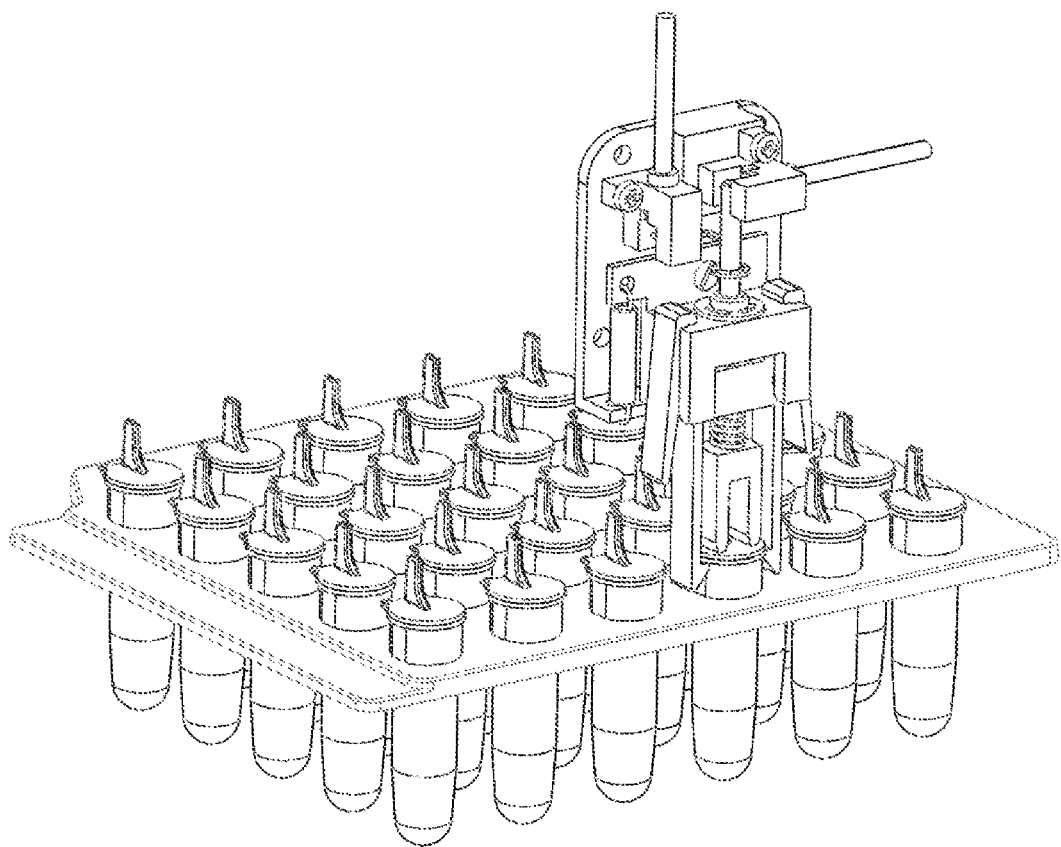
FIG. 6 shows grippers and robotic arm of FIGS. 6 and 7 on a picking position.

One other embodiment of a suitable gripper 44 is presented in FIGS. 4, 5, 6. First, the gripper itself is described with reference to FIG. 4. The gripper 44 has a body 41 wherefrom extends two symmetrically arranged hands 34 that have locking extensions 35 at their ends that are opposite to the body 41. The extensions 35 face towards each other and towards the central axis of the gripper 44. At the very end of the hands 34, the extensions 35 have a beveled surface 36 so that the tip 45 of the hand 34 is sharp and the extensions 35 move towards each other according to the bevel angle. The beveled surface 36 ends at a surface 37 that is parallel to the outer surface of the hands 34. In this embodiment, the beveled surface 36 may have a concave groove 38 starting from the tip 45 of the hand 34. The parallel surface 37 is flat for reasons explained later. The curvature of this groove 38 has preferably the same curvature and diameter as the stopping collar 16 of the tray 31 and the stopping collar 16 of the vessel 9. Alternatively, the groove 38 may have some other form, for example oval or V-shape. The hands 34 must have at least one open space between them in order to enable sideways movement of the pod 33 of the tray 31 or a vessel 9 between them. Therefore an embodiment with two hands is preferable.

The hands 34 are attached to the sides of an U-shaped body 41, that has an upper surface 52 on the opposite side of the hands and lower surface 53 between and on the side of the hands 34. The U-shape forms a recess 54. On the extensions of the U-shaped body 41 and on the same side as the hands is attached a pair of gripper claws 58 that comprise a handling grip 55 and a gripping tooth 56. The handling grips are attached at the central part of the handling grip 55 to the body 41 by flexible links 57. The attachment point of the link 57 divides the handling grip 55 into handling part and a gripping part. The position of the link on the length of the handling grip determines the lengths of the levers effecting to the flexible links 57.

Thus, the gripping force can be set by adjusting the flexibility and the lengths of the levers as necessary. The gripper 44 of FIG. 5 is made of a single piece of material. This enables to make it easy and cheap to produce, whereby it can be changed and disposed easily when needed. Also the design of the gripping part can be altered for gripping objects having different shape than disclosed herein.

In FIG. 5 the gripper is attached to a robotic arm 59 and a vessel 9 is attached to the gripper 44. The arm 59 includes an attachment block 60, that has an U-shape. The attachment block 60 is mounted on a tilt blade 61 that is mounted pivotally on the frame 62 of the robotic arm 59. The U-shaped body 41 of the gripper 44 is placed in the U-shaped recess of the attachment block 60. The attachment block 60 has grooves along the outer legs of the U and the flexible links 57 and the handling grips 55 set into these grooves. The gripping teeth 56 set above the attachment block 60. As can be easily contemplated from the drawing 5, the gripper can be detached from the robotic arm simply by pressing the handling grips 55. Their movement sets the teeth 56 free and the gripper 44 can be drawn downwards from the attachment block for detaching the gripper. Attachment is done simply by pushing a gripper 44 upwards on the block 60.

The robotic arm 59 disclosed herein has some features that should be disclosed. First is a collision sensor. This comprises a movable blade 61 attached to the frame 62 of the robotic arm 59 through a slide 63 and supported on its one edge by a spring element 64. On the opposite side to the spring element 64 of the blade 61 is a detector 66 that indicates the movement of the blade 61. The detector may be of any desirable kind, for example inductive, mechanical or photometric. Now, if the gripper 44 or a vessel carried thereon hits an obstacle in a vertical movement in direction of the hands 34, the movable blade 61 slides along the rail 63 and an indication is given by the detector 66.

Another detector is provided for detecting a presence of a vessel in the gripper 44. This detector comprises a feeler fork 67 that is attached to the attachment block 60 by a rod 68 that runs through the block 60 and above the upper surface thereof. A spring 69 is provided between the feeler fork 67 and the attachment block 60. At the opposite end of the rod 68 to the fork is a detector element 70, which may operate by any desirable method like the detector 66. Now, when a vessel is gripped, it is pushed between the hands 34 and simultaneously the feeler fork 67 is pushed upwards. When the vessel 9 clicks to its place between the hands 34, the fork stops. If the position of the fork is correct, detector 70 indicates correct gripping and presence of a vessel. Otherwise a malfunction indication is given. Such a feeler fork 67 with spring can be integrated to a detachable gripper (44) to have only one part.

Figure 3:
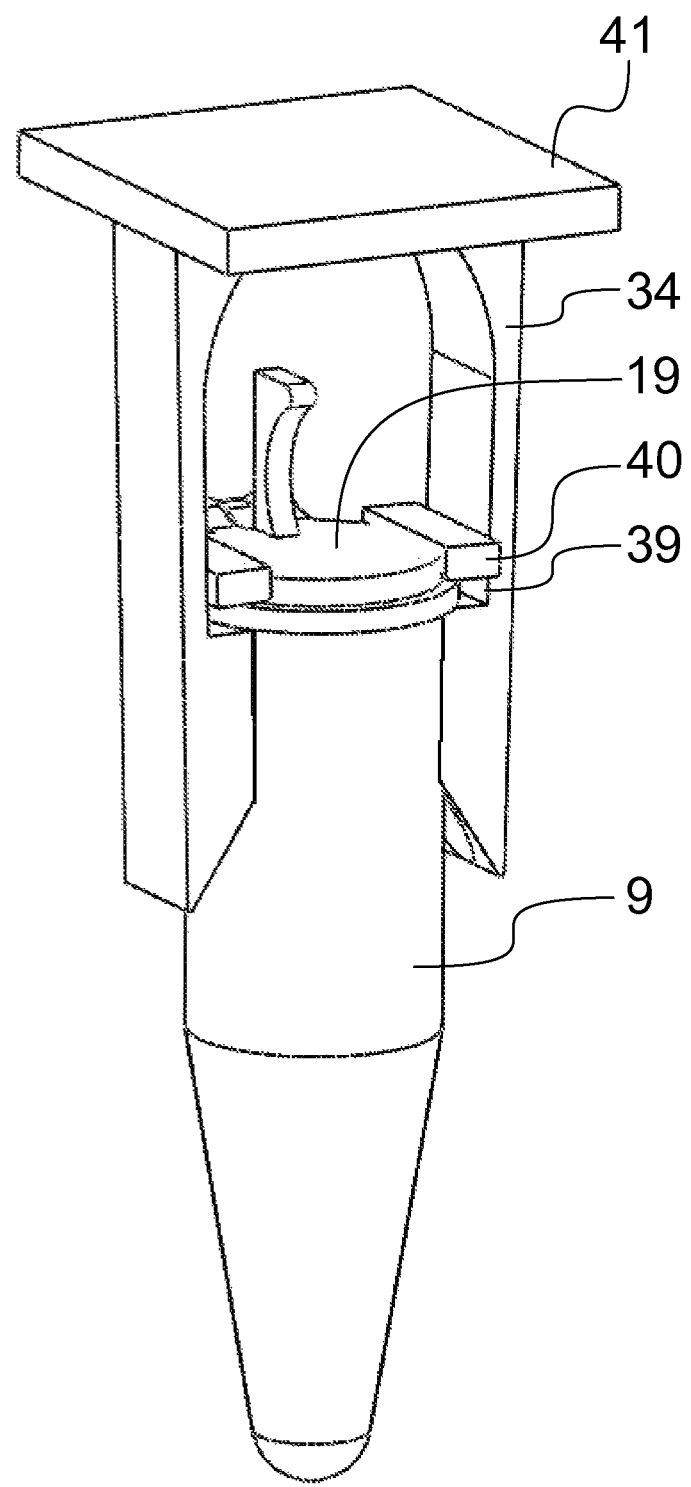
FIG. 3 is a side plan view of a gripper for transporting single reaction vessels and trays of reaction vessels according to one embodiment of the invention.

The gripper described above can be seen gripping a single vessel in FIGS. 3 and 5 and a vessel from a tray in FIG. 6. The point to be noted is that the depicted vessel 9 is an embodiment that has two flat surfaces 50, one on each side of the stopping surface 15. Now, since the corresponding surfaces in the gripper 44 are also flat, rotation of the vessel in the gripper 44 is prevented.

Figure 7:
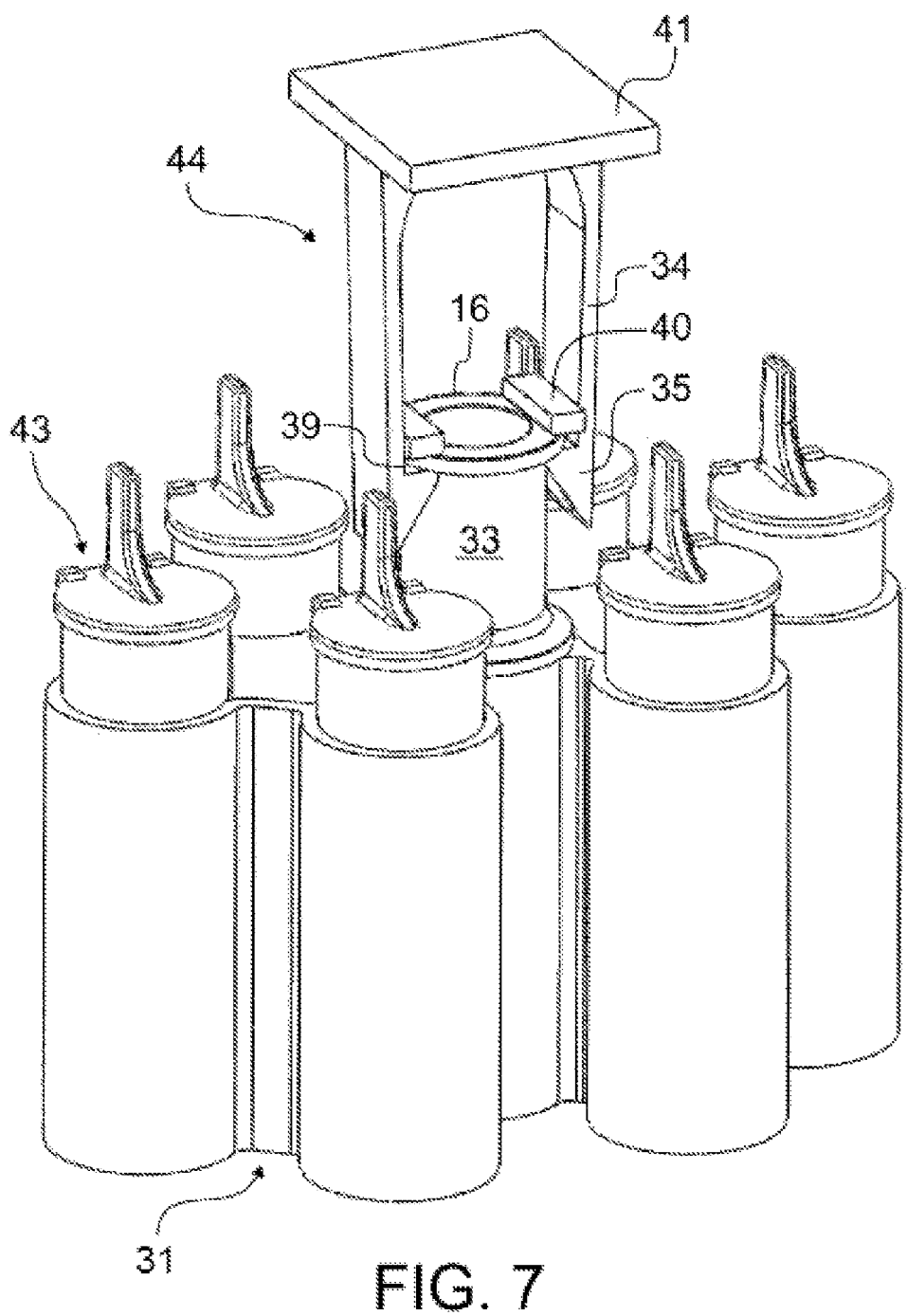
FIG. 7 is a side plan view of the tray of FIG. 2 with a gripper of FIG. 3 according to one embodiment of the invention.

The gripper 44 is used in a way that is shown in FIG. 7. In FIG. 7, the gripper 44 is attached to the gripping collar 16 of a pod 33 on a tray 31. The gripping of the pod 33 on the tray 29 is done simply by pushing the gripper 44 from above the pod 33 towards and over the gripping collar 16. The hands 34 of the gripper 44 are made to flex at least in a direction away from the center axis of the gripper 23. When pushed downwards towards the gripping collar 16, the beveled surfaces 36 push the hands 34 wider and the locking extensions 35 may be pushed over the gripping collar 16 of the pod 33. When the gripping collar 16 reaches the groove 39, the hands 34 snap over the gripping collar 16 and on the surface of the pod 33. The parallel parts 37 of the hands 34 set tightly on the pod 33 according to the form of the concave grooves 38 and lock the hands 34 sideways over the pod 33. In the vertical direction, the movement is stopped by stoppers 40 on the gripper 44. Gripping of a single reaction vessel 9 is similar.

After one of the tray 31 or vessel 9 is gripped or engaged, it can be transported to another position within the automated chemical analyzer wherever it is needed. After transportation, the gripper 44 has to be disengaged to release the tray 31 or vessel 9. This is done simply by moving the gripper 44 sideways in view of the center axis of the pod 33 or reaction vessel 9 and away from the open space between the hands, whereby the hands 34 of the gripper 44 flex and release the tray 31 or vessel 9 from the grip of the gripper 44.

The form of the gripping collar 16, is preferably circular. It can be contemplated that the collar 16 is made rectangular or polygonal. These embodiments would seemingly work, but the structure would be more difficult to manufacture and use. The hands 34 can be made flexible by using suitable material and dimensioning or by using a spring mechanism, for example. Such a spring mechanism could have sideways movable grippers that would attach to a groove on a vessel. The grip could be loosened by mechanical activator.

Thus, while there have been shown and described and pointed out fundamental novel features of the invention as applied to a preferred embodiment thereof, it will be understood that various omissions and substitutions and changes in the form and details of the method and assembly may be made by those skilled in the art without departing from the spirit of the invention. For example, it is expressly intended that all combinations of those elements which perform substantially the same results are within the scope of the invention. Substitutions of the elements from one described embodiment to another are also fully intended and contemplated. It is also to be understood that the drawings are not necessarily drawn to scale but they are merely conceptual in nature. It is the intention, therefore, to be limited only as indicated by the scope of the claims appended hereto.

What is claimed is:

1. An assembly for transporting single and multiple reaction vessels, comprising:
    at least one reaction vessel,
    at least one gripper,
    a transport device, and
    a gripping collar on the reaction vessel for the gripper to engage the reaction vessel,
    wherein said at least one gripper comprises
        a gripper body,
        two flexible hands attached to and extending below the gripper body and separated by an open space to enable the gripping collar to pass therebetween upon flexing of the two flexible hands in a direction away from a center axis of the gripper;
        two gripper claws extending above the gripper body for releasably attaching the gripper to the transport device, each of the two gripper claws being attached to the body by respective flexible links, wherein each flexible link is attached to a respective one of the two gripper claws at a central part of the gripper claw between an upper end and a lower end of the gripper claw;
    wherein the two flexible hands are configured to snap over and carry the gripping collar; and
    wherein each of the two gripper claws is configured to pivot about the respective flexible link that attaches the gripper claw to the body to attach or detach the gripper from the transport device when the two flexible hands are snapped over the gripping collar.

2. The assembly according to claim 1, wherein the gripping collar is circular.

3. The assembly according to claim 1, wherein the vessel includes a circular stopping collar having a diameter smaller than the circular gripping collar and having a width.

4. The assembly according to claim 1, wherein the hands have locking extensions that have grooves for gripping a circular surface.

5. The assembly according to claim 1, wherein the hands have locking extensions that have flat surfaces for gripping a flat surface.

6. The assembly according to claim 1, wherein the gripper is made of a single piece of material.

7. The assembly according to claim 1, wherein the flexible hands have locking extensions that have grooves for gripping a circular surface.

8. The assembly according to claim 2, wherein the flexible hands have locking extensions that have grooves for gripping a circular surface.

9. The assembly according to claim 3, wherein the flexible hands have locking extensions that have grooves for gripping a circular surface.

10. The assembly according to claim 1, wherein the flexible hands have locking extensions that have flat surfaces for gripping a flat surface.

11. The assembly according to claim 2, wherein the flexible hands have locking extensions that have flat surfaces for gripping a flat surface.

12. The assembly according to claim 3, wherein the flexible hands have locking extensions that have flat surfaces for gripping a flat surface.

13. The assembly of claim 1 wherein a lower end of each of the two flexible hands includes a locking extension that extends into the open space between the hands, and each of the locking extensions has a downward facing beveled surface configured to urge the locking extension and respective flexible hand to flex away from the center axis of the gripper when the gripper is pushed downwards over the gripping collar.

14. The assembly of claim 1 wherein the body is rigid and each gripper claw is pivotable about a respective flexible link independently of the two flexible hands such that the gripper is configured to be attached or detached from the transport device without moving the flexible hands.

* * * * *